Figure 1:
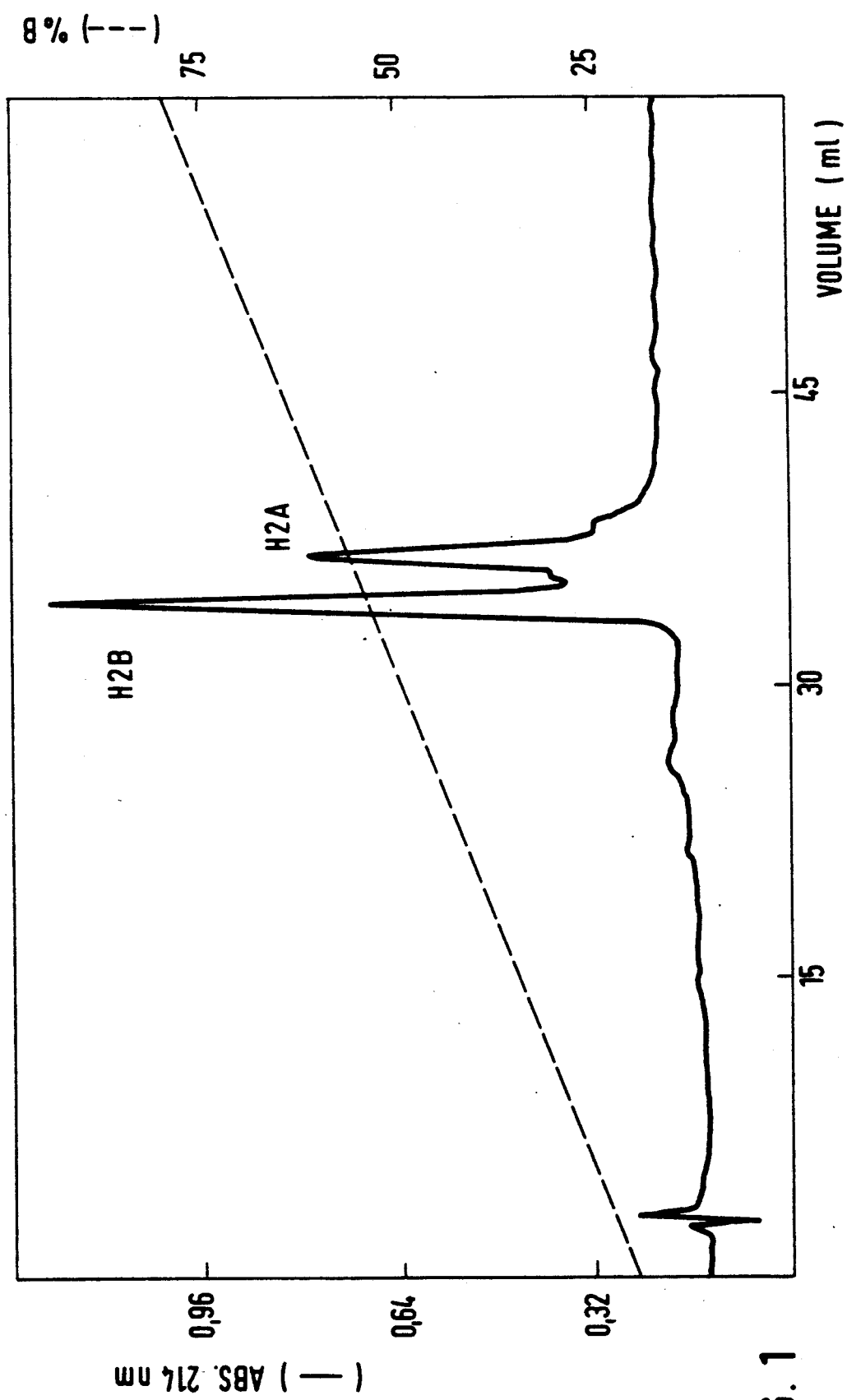

United States Patent [19]

Zeppezauer et al.

[11] Patent Number: 5,182,257
[45] Date of Patent: Jan. 26, 1993

[54] USE OF PURE HISTONES H1 AND H2A:H2B DIMERS IN THERAPEUTIC METHODS

[75] Inventors: Michael Zeppezauer, Saarbrücken-Scheidt; Robert Reichhart, Homburg/Saar, both of Fed. Rep. of Germany

[73] Assignee: Volker Rusch, Fed. Rep. of Germany

[21] Appl. No.: 332,658

[22] Filed: Apr. 3, 1989

Related U.S. Application Data

[63] Continuation-in-part of Ser. No. 777,783, Sep. 12, 1985, Pat. No. 4,818,763.

[30] Foreign Application Priority Data

Feb. 16, 1984 [DE] Fed. Rep. of Germany ....... 3405620
Dec. 1, 1984 [DE] Fed. Rep. of Germany ....... 3400928

[51] Int. Cl.$^5$ .................... A61K 37/00; A61K 37/08; C07K 13/00
[52] U.S. Cl. .......................................... 514/2; 530/358
[58] Field of Search ..................... 514/2, 885; 530/358

[56] References Cited

U.S. PATENT DOCUMENTS

| | | | |
|---|---|---|---|
| 4,124,700 | 11/1978 | Goldstein | 424/1 |
| 4,767,714 | 8/1988 | Shalitin | 435/272 |
| 4,818,763 | 4/1989 | Rusch et al. | 514/2 |
| 4,902,505 | 2/1990 | Pardridge et al. | 424/85.7 |

OTHER PUBLICATIONS

Matsukawa et al., J. Biochem., vol. 98, (1985), pp. 695–704.
Rudinger et al., Peptide Hormones, University Park Press, edited J. A. Parsons, pp. 1–7, Jun. 1976.

*Primary Examiner*—Merrell C. Cashion, Jr.
*Assistant Examiner*—A. M. Davenport
*Attorney, Agent, or Firm*—Rosenman & Colin

[57] ABSTRACT

The invention relates to the use of pure histones H1, H2A, H2B, H2A:H2B, H3 as hormonal or hormon-like active substance for the preparation of pharmaceuticals for the immuno-therapy, for the therapy of endocrine disturbance and for cancer therapy. Instead of the histones also their evolutionary variable sections or at least one partial section of at least five aminoacid residues of at least one evolutionary variable histon section can be used.

9 Claims, 13 Drawing Sheets

FIG. 2  HTH – CONCENTRATION

▲——▲  50 μg/ml
□——□  100 μg/ml
●——●  125 μg/ml
△——△  150 μg/ml
■——■  200 μg/ml
○----○  CONTROL

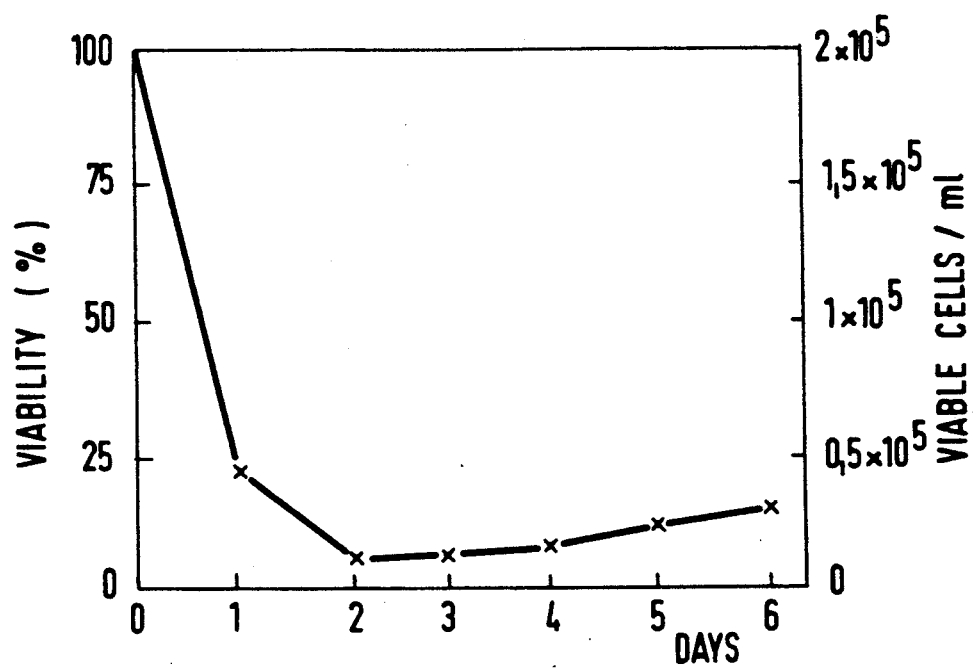
FIG. 7   CANCER CELL LINE DAUDI
(BURKITT-LYMPHOMA)
H1-CONCENTRATION : 250 µg / ml
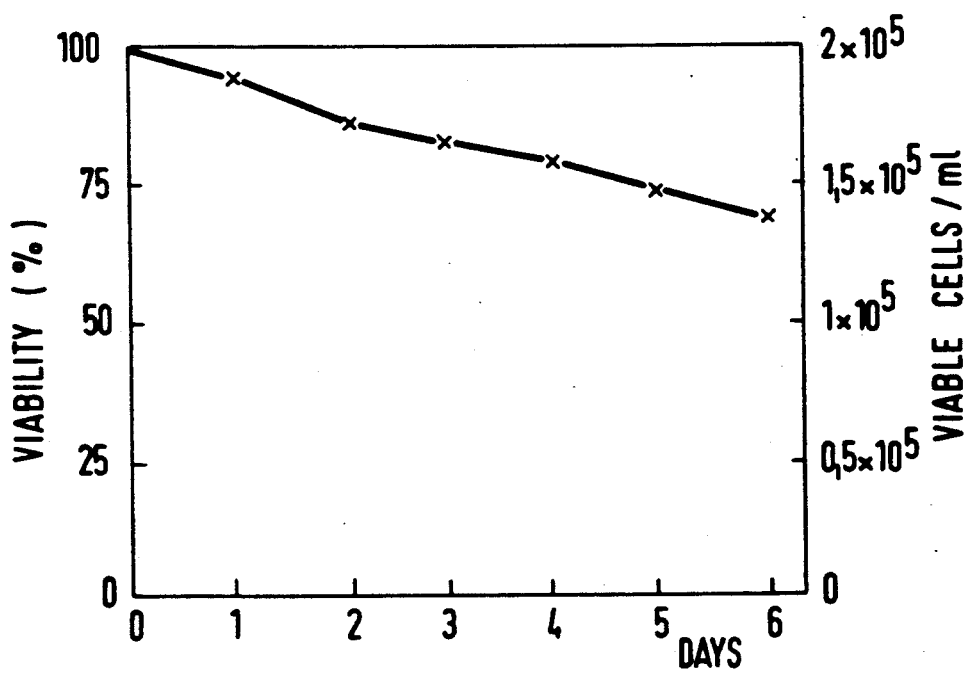
FIG. 8   CANCER CELL LINE EB 2
(BURKITT-LYMPHOMA)
H1-CONCENTRATION : 250 ug / ml

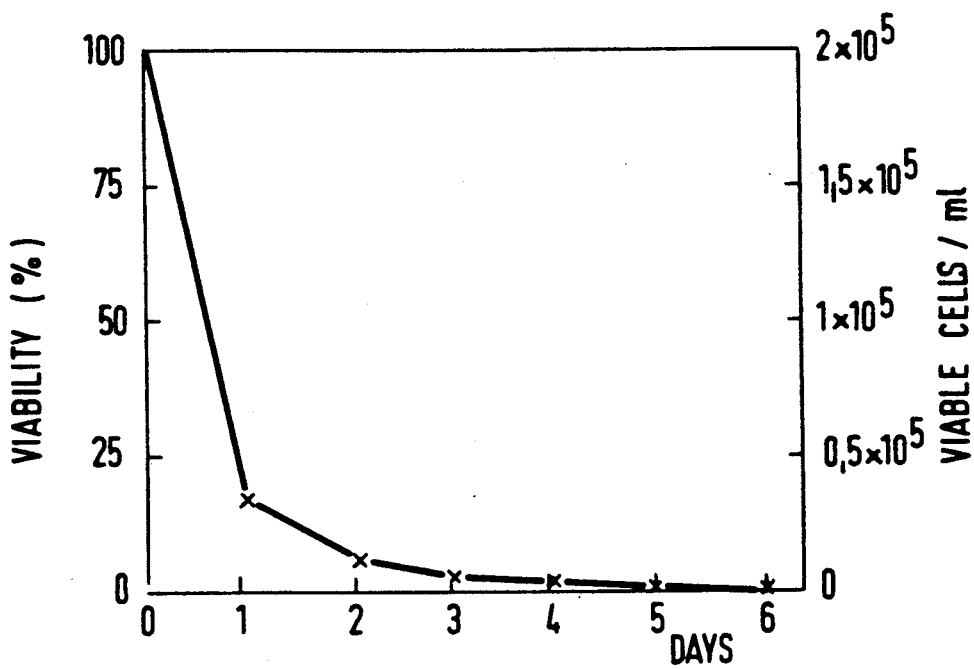
FIG. 9  CANCER CELL LINE IM 9
(MULTIPLE MYELOMA)
H1 - CONCENTRATION : 180 µg / ml
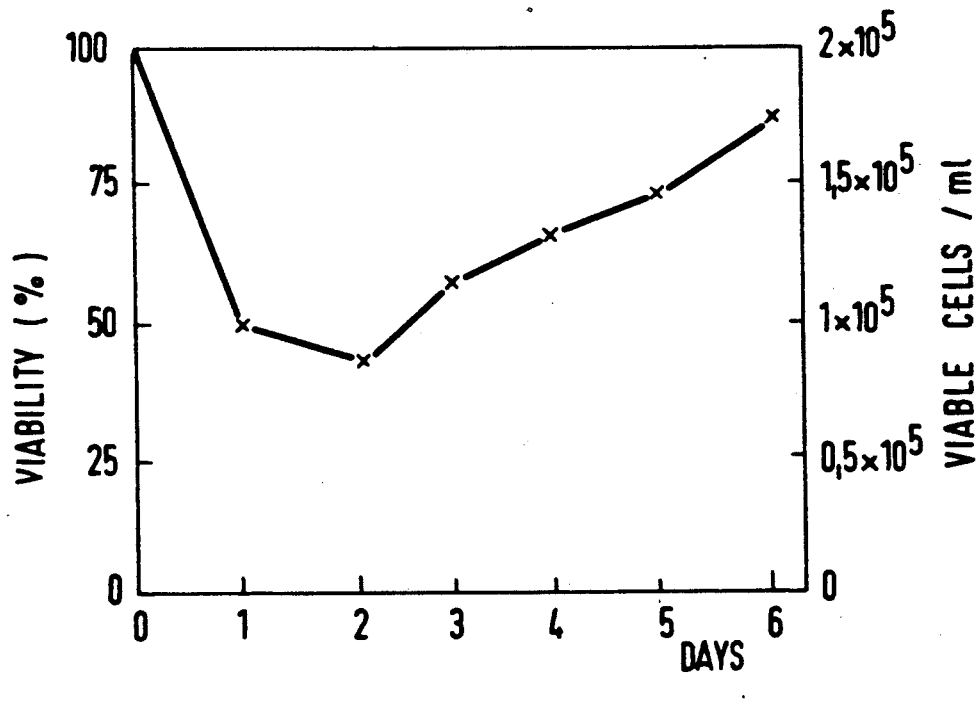
FIG. 10  CANCER CELL LINE CCRF SB
(ACUTE LYMPHOBLASTIC LEUKEMIA)
H1 - CONCENTRATION : 250 µg / ml

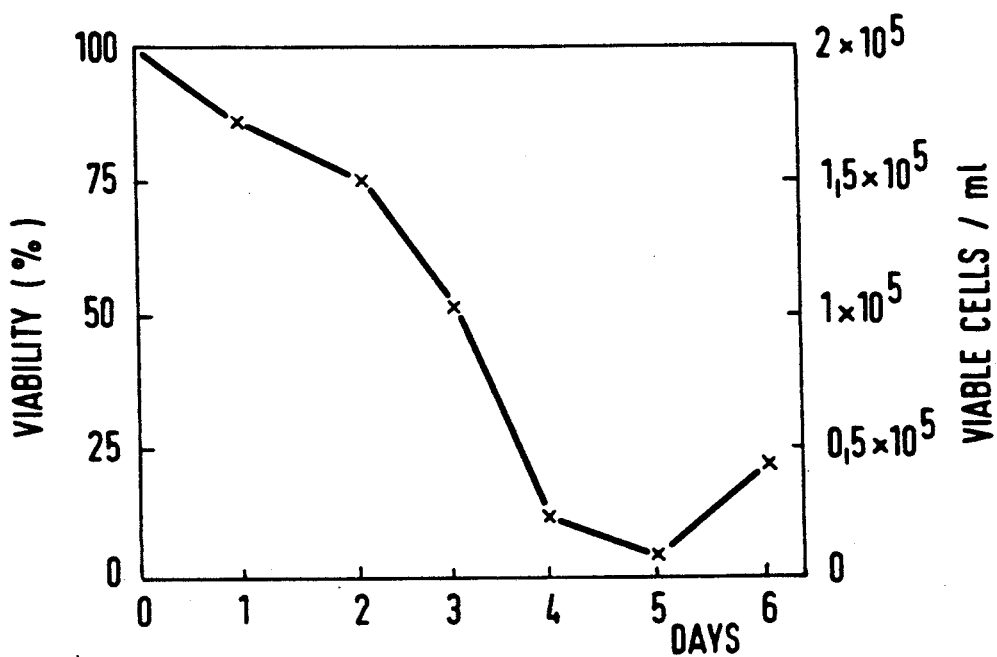
FIG. 11  CANCER CELL LINE CCRF CEM
(ACUTE LYMPHOBLASTIC : LEUKEMIA)
H1 − CONCENTRATION : 250 µg / ml
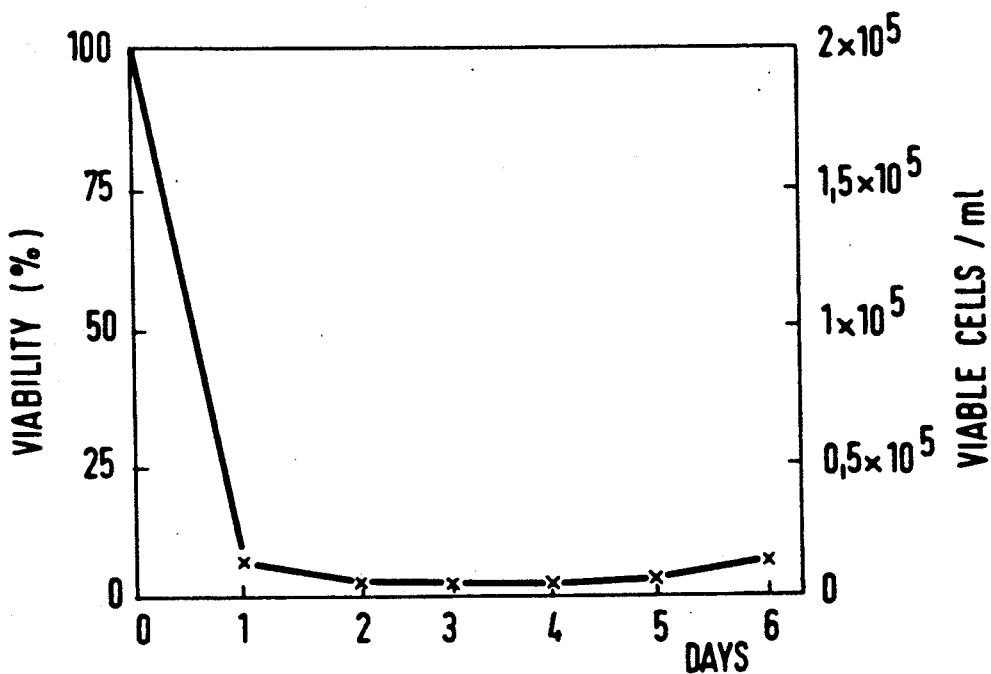
FIG. 12  CANCER CELL LINE NAMALWA
(BURKITT- LYMPHOMA )
H1 − CONCENTRATION : 250 µg / ml

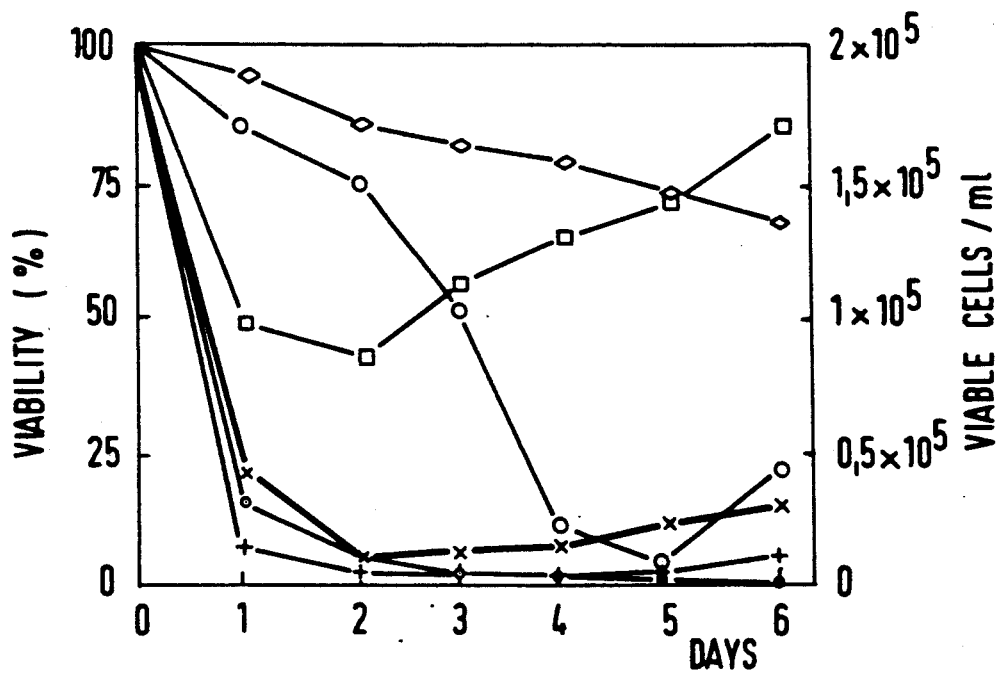
FIG. 13  SUMMERY OF THE FIGURES 7 – 12
H1 – CONCENTRATIONS : 250 μg / ml
( LMO 180 μg / ml )
×——× DAUDI
◇——◇ EB 2
•——• IM 9
□——□ CCRF SB
○——○ CCRF CEM
+——+ NAMALWA

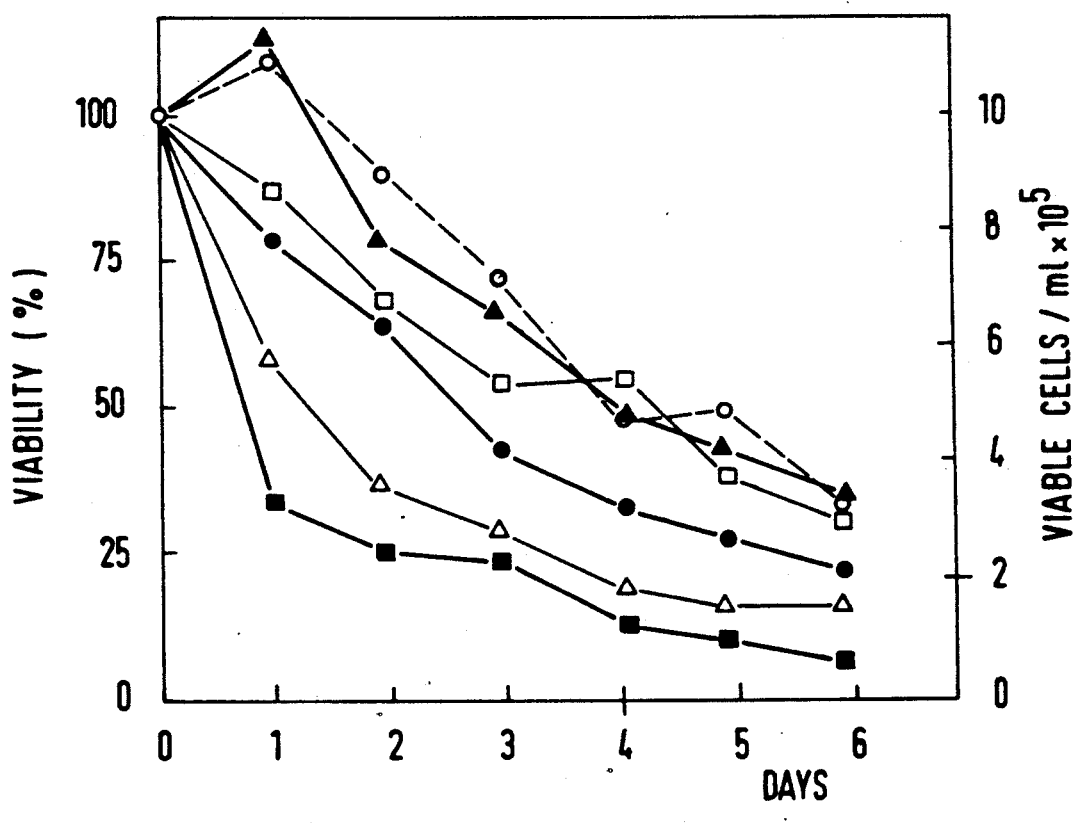
FIG. 14 VIABILITY OF NORMAL MURINE SPLEEN CELLS AS A FUNKTION OF H1- CONCENTRATION
▲——▲ 50 μg/ml
□——□ 100 μg/ml
●——● 125 μg/ml
△——△ 150 μg/ml
■——■ 200 μg/ml
○----○ CONTROL

USE OF PURE HISTONES H1 AND H2A:H2B DIMERS IN THERAPEUTIC METHODS

This application is a continuation-in-part application of pending U.S. patent application Ser. No. 777,783 filed in the United States Patent Office on Sep. 12, 1985 and now U.S. Pat. No. 4,818,763 entitled "Biologically Active Substance with Hormonal Properties, Production Process Thereof and Utilization of Histones for Medical Purposes".

According to the present state of knowledge histones H1, H2A, H2B, H3 and H4 are the essential components to the cell nucleic and are together with DNA the substantial components of chromatin.

The invention is based on the discovery that histones has hormonal or hormone-like and immuno-stimulating functions. Such functions so far have never been brought in connection with histones. For the experts it was novel and surprising that the histones are freely moving in the blood circulation and the lymphatic system of healthy organisms and will bring about a biological response due to the interaction with specific receptors of living cells.

In U.S. Pat. No. 4,451,553 it is proposed to prepare an antigen from human or animal cancer cells, which is injected to persons or animals suffering from cancer in order to incite the production of antibodies, which are not only intended to destroy the antigens but also the very own cancer cells. From the cancer cells a malignant total histone is being isolated, which is not divided into the individual histones, and the total histone is bonded to malignant DNA and RNA in order to form the antigen.

In "Chemical Abstracts" 72, 109724 (1970) it was proposed to isolate fragments of the histones which are rich with arginine and lysine, to charge these fragments with reactive groups and to take advantage of their bondage to nucleic acids for chemically changing the nucleic acids by means of said reactive groups. Said literature discloses the idea of using specific histone fragments as a carrier for chemotherapeutic substances applied in the treatment of cancer.

In "Chemical Abstracts" 74, 85743 (1971) it is said that the resulting total histone fraction will prevent the formation of antibodies against $T_2$-bacteriophages if given simultaneously with the antigen (the phage) and furthermore in very large doses (50 mg/kg).

In Chemical Abstracts" 73, 96837 (1970) the immunosuppressive effect of total histone is described by the example of a human skin transplantation.

The above mentioned state of the art neither discloses nor suggests the discovery of the inventors that pure histones H1, H2A, H2B, H3 and the pure histone dimer H2A:H2B have hormonal or hormone-like and immuno-stimulating functions.

It is the problem of the invention to provide effective pharmaceuticals for specific therapeutic purposes on the basis of this discovery.

The problem is solved by using at least one of the pure histones H1, H2A, H2B, H2A:H2B, H3 or at least a partial section of at least five amino acid residues of the evolutionary variable histone section (amino-acid residues 1 to 30) of the histones as a hormonal or hormone-like active substance for the preparation of pharmaceuticals used in immunotherapy, the therapy of endocrine disturbances and in cancer therapy.

It is an advantage of the pharmaceutical according to the invention that it can be used for the treatment of cancer and radiation induced leukemia, AIDS-diseases, for dampening the function of the suprarenal cortex, the thyroid, of the gonads, for supporting the function of the hypophysis and for the treatment of after-effects resulting from the removal of the thymus gland (thymectomy).

In the following examples the therapeutic efficiency of the pharmaceutical according to the invention is shown. The active substance of the examples 1 to 4 is the histone dimer H2A:H2B according to FIG. 1. It is very likely that positive effects will also be achieved with histone H2A alone or with histone H2B alone.

As is generally known, the active components of the histones H2A:H2B are their evolutionary variable sections. Therefore it is likely that an effect according to the invention can also be achieved with at least one evolutionary variable histone section of the histones H2A and H2B. It is furthermore known that with an effective polypeptide at least a partial effect can already by achieved when there is a partial section of at least five aminoacid residues. Therefore it is probable that an effect according to the invention can already by achieved with a partial section of at least five aminoacid residues of at least one evolutionary variable histone section of the histones H2A and/or H2B.

The active substance H2A:H2B according to the invention (FIG. 1) was prepared by the inventors from a thymus preparation (homeostatic thymus hormone) from calf thymus according to Comsa & Bernardi ("Extraction, Fractionation and Testing of Homogenous Thymic Hormone Preparation", Anals of the New York Academy of Sciences, vol. 240, pages 402-403, Feb. 28, 1975) by means of high speed liquid chromatography. Further details will follow in experiment 1. In the same manner pure H2A and pure H2B can be prepared. It will still have to be clarified whether the active substance H2A:H2B (FIG. 1) is a mixture of H2A and H2B or whether it is a compound of H2A and H2B (H2A:H2B complex). The invention therefore is not restricted to the use of H2A:H2B, but also extends to their active components (smallest active part=at least one section of five aminoacid residues of an evolutionary variable histone section of H2A or H2B).

In "Thymic Hormones", pages 59-96, University Park Press, Baltimore, Comsa demonstrates that their homeostatic thymus hormone (HTH) has multiple interrelationships with several glands of endocrine systems. So it was possible to show that there is an antagonism with the hormones thyroxine, ACTH, desoxycorticosterone and gonadotropine and that there is a synergistic effect with the growth hormone. In "Ann. J. Med. Sci." (1965) 250, pages 79-85, J. Comsa was furthermore able to demonstrate that his homeostatic thymus hormone (HTH) completely suppresses the immunological consequences of thymectony. In mice the development of radiation induced leukemia after sublethal doses of X-ray was prevented by HTH, see J. Comsa et al., "C. R. Acd. Sci. Paris" (1979) 288, pages 185-187.

With mice from the inbred strain C57 b1 exposed to X-ray before the protective effect began when the animals were daily given a subcutane injection of HTH after the last one of 4 sublethal radiations. Latent period and life expectancy of the animals depended on the dose of HTH given. With about 100 µg of HTH per animal and day all animals stayed healthy, whereas the check group died of leukemia after 9 months.

As shown by the following experiments the inventors were able to prove that the histone fraction H2A:H2B from the homeostatic thymus hormone (HTH) can be used for cancer therapy. According to the inventors the effects of HTH as found by J. Comsa et al. at least in part result from the histones H2A, H2B, so that they probably are not only suited for cancer therapy, in particular the treatment of malignant cancer of lymphoma cells, but also for the immunotherapy (e.g. AIDS-disease) and for the therapy of endocrine disturbances.

The concentrations of H2A:H2B to be given will be between 50 and 500 μg/l. They will be given especially by subcutane or intrasmuscular injection. Said injections preferably are physiological salines with may be phosphate-buffered and which contain H2A and/or H2B or their active components.

It is a substantial advantage of the use of the active substance according to the invention over the above mentioned homeostatic thymus hormone (HTH) that said active substance is defined precisely and can be represented purely and without foreign components in various manners, also including gene technology, which cannot be done with HTH.

EXAMPLE 1

The efficiency of H2A:H2B was tested in vitro with myeloma cells (cancer cell line P3Ag8.653, Flow Laboratories) of the mice inbred strain BALB/c. Said subklon of the foregoing cancer cell line adheres to the bottom petri dishes because of long-term cultivation and selection.

There are no immunoglobulines preticipated, it does not grow in HAT-medium and easily amalgamates with spleen cells.

The cultivation of the cancer cells took place in a culture medium of:

| | |
|---|---|
| RPMI 1640 with L-glutamine without NaHCO$_3$ | 10.39 g/l |
| Penicilin G | 2 × 10$^4$ int. units |
| Streptomycin sulfate | 2 × 10$^4$ int. units |
| L-Glutamine | 1% 200 mM |
| Pyruvate | 1% 200 mM |
| NaHCO$_3$ | 0.2% |
| β-Mercaptoethanol | 1% 5 × 10$^{-3}$ M |
| Fetal calf serum (= FCS) of Biochem, Berlin | 10% |
| pH-value | 7.2 |

The H2A:H2B used was prepared from a purified histone preparation from calf thymus by means of high speed liquid chromatography (FIG. 1). The elution was carried out at a μBondapak C-18-column with a linear gradient (%B) of 20 to 80% acetonitrile in 0.1% trifluoroacetic acid with a flow of 1 ml/min. The absorption was measured at 214 nm. In FIG. 1 the abscissa shows the volume in ml, the left ordinate shows the absorption at 214 nm and the right ordinate shows the linear gradient (%B).

The cells are fed with completed culture medium (RPMI 1640 with 10% FCS). The culture medium was renewed each day. When the bottom of the culture dish was fully overgrown the cells were scrapped off and part of them was transplanted, as for the tests cells in their optimum environment for growth were needed. Breeding was performed at 36.5° C. and 5.5 CO$_2$ in an incubator.

The concentration of viable cells was determined with the coloring agent Nigrosin (0.2% in phosphate-buffered saline (PBS) in the Neubauer-counting chamber.

Completed culture medium was added to freeze-dried H2A:H2B concentration (storage at −20° C.) and filtered under sterile conditions. (Sterivex-Filter System GV of Millipore, Munich). With 400 μg/ml the concentration of H2A:H2B was twice as high as the highest concentration needed for the experiment. For lower concentrations the solution was diluted accordingly.

For the experiment cells were scraped off from the bottom of not too thickly grown culture dishes, the number of living cells was determined and adjusted to 3.5×10$^5$ cells/ml. 100 μl H2A:H2B solution or a thinner were added to 100 μl of said cell suspension and incubated in an incubator. The final concentration of the cells per dish was 1.75×10$^5$ cell/ml with a concentration of H2A:H2B of 200, 150, 125, 100 and 50 μg/ml. The experiment was carried out for 6 days, the viable cells were counted once a day, in the first two days twice a day. For each concentration therefore eight starting preparations were needed.

Figure 2:
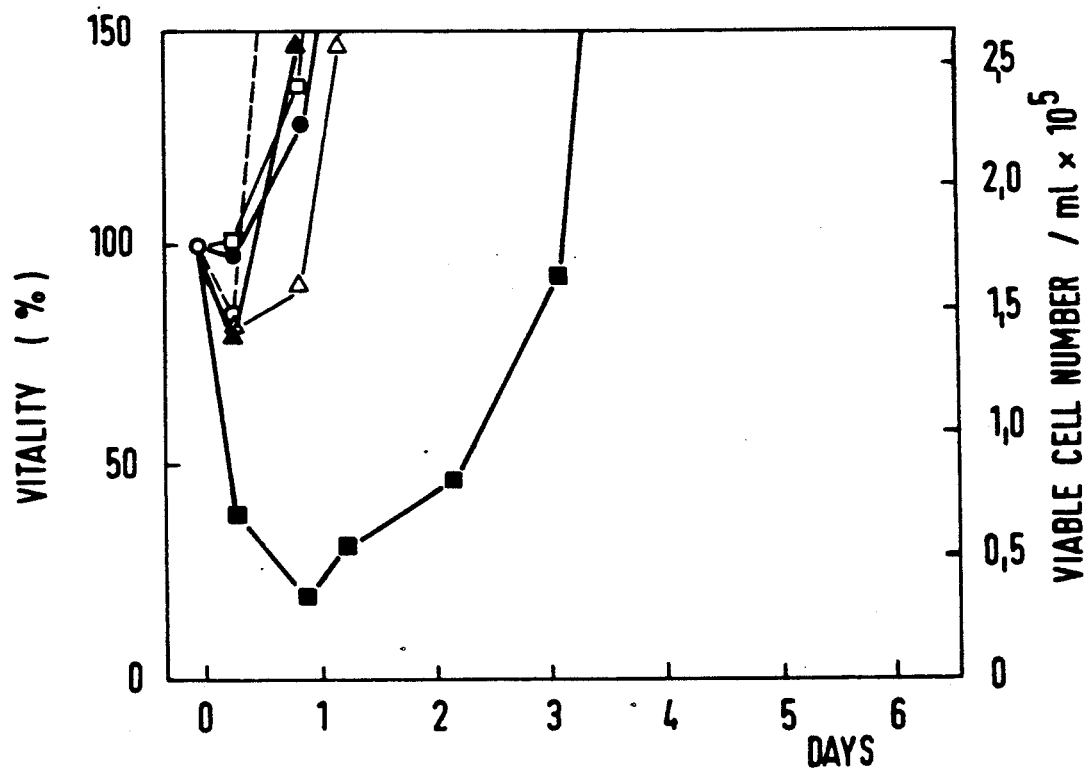

In FIG. 2 the viable cell concentration (=viable cell number/ml) and the vitality are graphically compared to time (period of incubation). The vitality relates to the originally used cell concentration (1.74×10$^5$ cells/ml=100%):

$$\text{vitality (\%)} = 100 \times \frac{\text{viable cell concentration}}{1.74 \times 10^5 \text{ cells/ml}}$$

In all concentrations H2A:H2B shows a cytotoxic effect to the tested cancer cell line, the efficiency, however, is different.

In FIG. 2 the timely course of the vitality and the vaible cell number/ml of the cancer cells on incubation with different concentrations of H2A:H2B is shown graphically. Concentrations up to 150 μg/ml of H2A:H2B did not show any or only an inferior retardation of the cell growth. With a concentration of 200 μg/ml of H2A:H2B the killing rate was 80% at the first day. Subsequently the cells continued growing like in the other concentrations used and like in the check concentration. The initial number was reached after about three days.

EXAMPLE 2

The efficiency of H2A:H2B was furthermore tested in vitro at a human cancer cell line. It was the cancer cell line IM-9 from the marrow of a female patient with multiple myeloma which was used. For B-cells said cancer cell line has receptor positions for human growth hormones, for insulin and calcitonin.

Description and origin of the cancer cells:

Growth properties: 4–5-fold doubling within 5–7 days with an initial number of cells of 3–4×10$^5$ of viable cells/ml Morphology: Lymphoblast-like Karyology: Chromosome frequence distribution 50 cells 2/43; 6/45; 36/46; 5/47; 1/48 2n=46 human, female, stemline number=46; dipoid, stable Karyotype Sterility: Test for mycoplasma, bacteria and fungi was negative Reverse transcriptase: negative Surface immunoglobulines: detected EBNA: positive Submitted: D. N. Buell, NIH, Bethesda, Md. U.S.A.

Prepared and characterized: American Type Culture Collection, Rockville, Md.

Literature: Buell D. N., (1972) Ann. N.Y. Acad. Sci. 190, 221-234; Proc. Natl. Sci. U.S.A. 71, 84-88 (1974); J. Biol. Chem. 249, 1661-1677 (1974).

For control freshly isolated spleen cells from mice inbred strains BALB/c were used. The cells were kept in culture under sterile conditions at 37° C., 5.5% $CO_2$ and 95% of relative humidity. As medium RPMI 1640 with 10% fetal calf serum of Biochrom, Berlin, was used.

To the culture medium (according to experiment 1) H2A:H2B (according to experiment 1) with a final concentration of 180 μg/ml was added. $2 \times 10^5$ viable cells were cultivated in said medium and the total cell number and the number of viable cells were counted daily. For this purpose one part of a solution of 0.1 mg acridine orange and 0.1 mg ethidium bromide in 100 ml phosphate buffered physiologic saline (PBS) were mixed with an equal volume of cell suspension and evaluated immediately under a fluorescence microscope. Living cells take up acridine orange and appear green when a blue excitation is used, whereas ethidium bromide diffuses into dead or dying cells and turns the cells into orange. When a green excitation is used, living cells are not turned into color, whereas dead cells appear red.

H2A:H2B originates form a purified histone preparation according to experiment 1.

Figure 3:
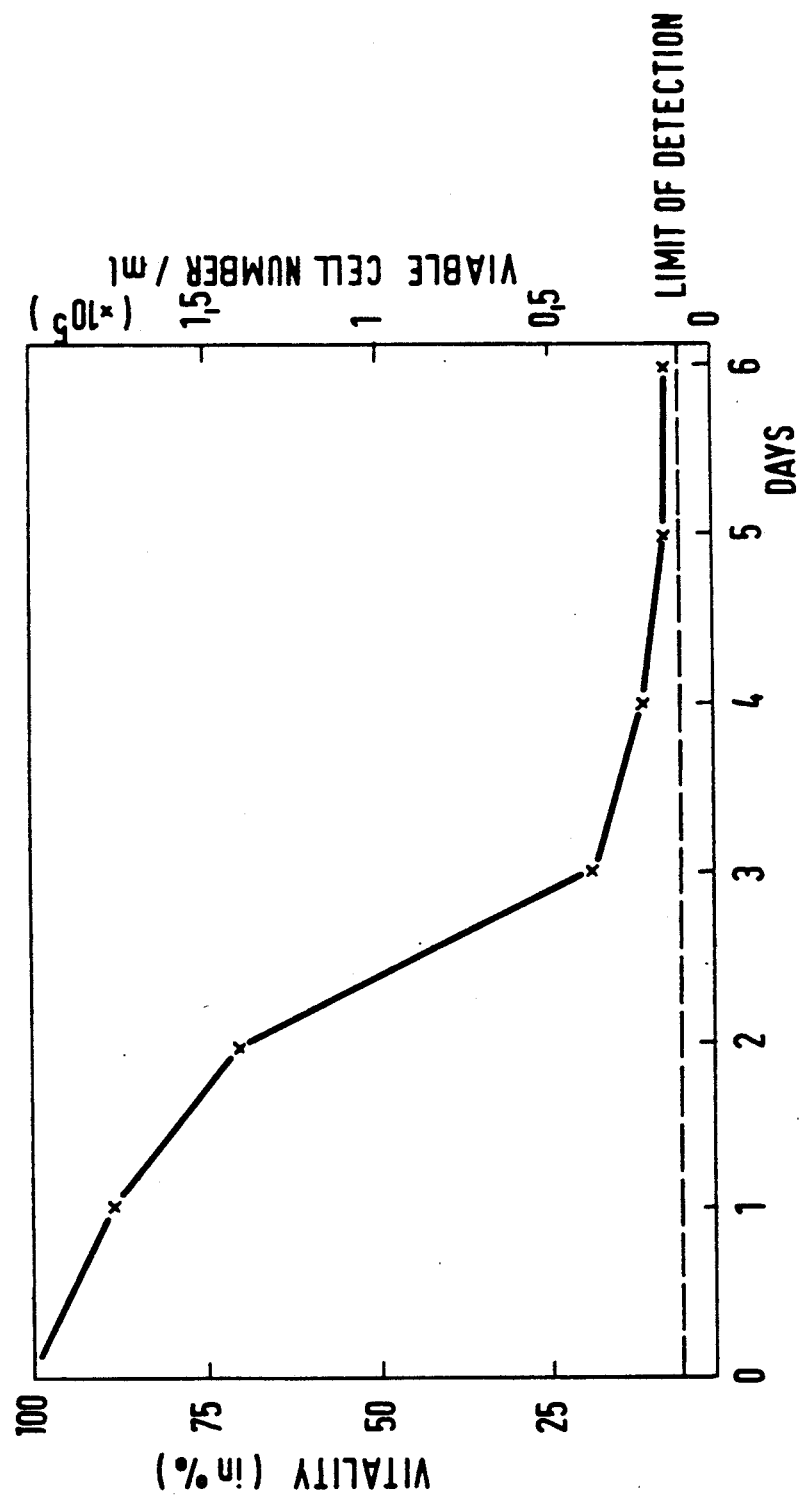

The timely course of the vitality and/or the viable cell number/ml of the human tumor cell line IM-9 after a single dose of 180 μg H2A:H2B/ml cell suspension is shown in FIG. 3. The viable cell number was determined under a fluorescence microscope by means of the vital coloring agents acridin-orange and ethidium bromide.

Already after a single dose of 180 μg of HTH is given to a cell suspension with $2 \times 10^5$ cells/ml the number of viable cells reduced by more than 80% within 3 days. This reduction was continued with more than 90% of killed cells up to the 6th day of the experiment. Within the test period of 7 days no growth of the rest of the surviving cells was observed, which corresponds to a complete breakdown of the cancer cells. The number of untreated cancer cells has become fourfold as high as in the beginning of the experiment. Not degenerated spleen cells treated with 180 μg HTH/ml ($2 \times 10^5$ ml) showed a nonsignificant higher death rate in the same period of time.

After a single dose of H2A:H2B a selective killing of the human cancer cell line IM-9 follows. With a dose of 180 μg/ml of medium the human multiple lyelom line with a cell density of $2 \times 10^5$/ml has a complete breakdown, whereas the normal spleen cells from BALB/c mice only show an insignificant increase in the natural death rate.

In the following examples the therapeutic efficiency of the pharmaceutical according to the invention for cancer therapy is shown. The active substance is a H2A:H2B histone mixture or histone complex according to FIG. 1. It is very likely that positive effects can also be achieved with a histone H2A alone or with as histone H2B alone.

The comparison of the sequences with known thymic hormons shows that the hormonal or hormonal-like active components of the histones are their evolutionary variable sections. Therefore it is probable that an effect according to the invention can also be achieved with at least one evolutionary variable histone section of the histones H2A and H2B. It is furthermore known that at least a partial effect may be achieved already when a partial section of at least five amino acid residues is present. Therefore it can be assumed that an effect according to the invention can already be achieved with one partial section of at least five aminoacid residues of at least one evolutionary variable histone section of the histones H2A and/or H2B.

This makes it evident that H2A:H2B does not only retard the growth of malignant lymphom cells but can entirely kill the cells. Comparable successes so far have not been achieved with the cytostatics, such as cyclophosphamide, as presently used for chemotherapeutics, which do also kill normal, not degenerated cells and cause heavy secondary effects in clinical use. While H2A:H2B in a concentration of 180 μg/ml makes completely disappear malignant lymphom cells: healthy lymphatic cells are only insignificantly influenced in their growth.

If H2A:H2B can kill lymphom cells, then also other kinds of cancer cells, as e.g. carcinomes, melanomes, andenomes should be treatable with H2A:H2B, whereby the growth retardations in specific periods and with specific doses will probably be different.

EXAMPLE 3

Figure 4:
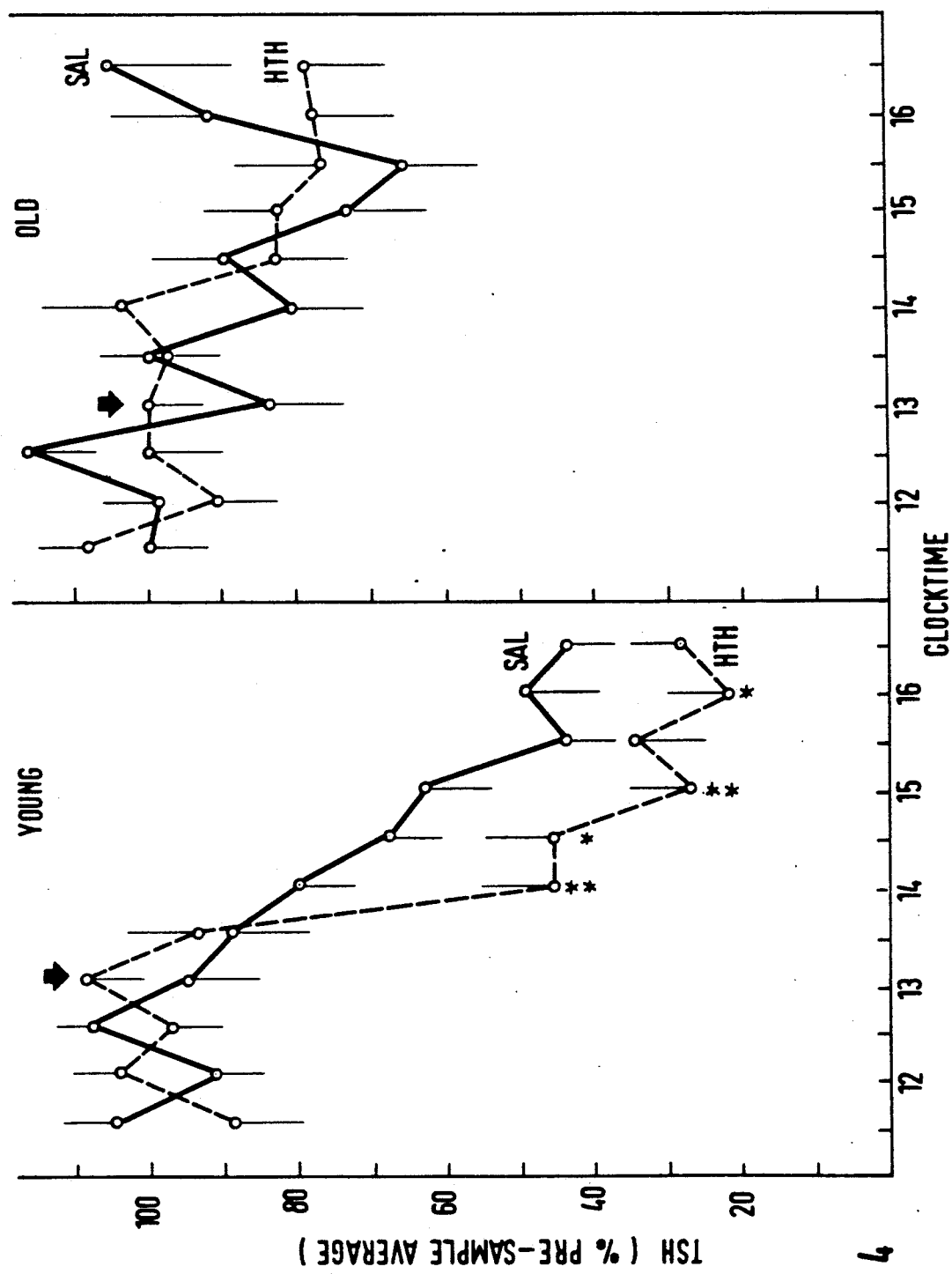
Figure 5:
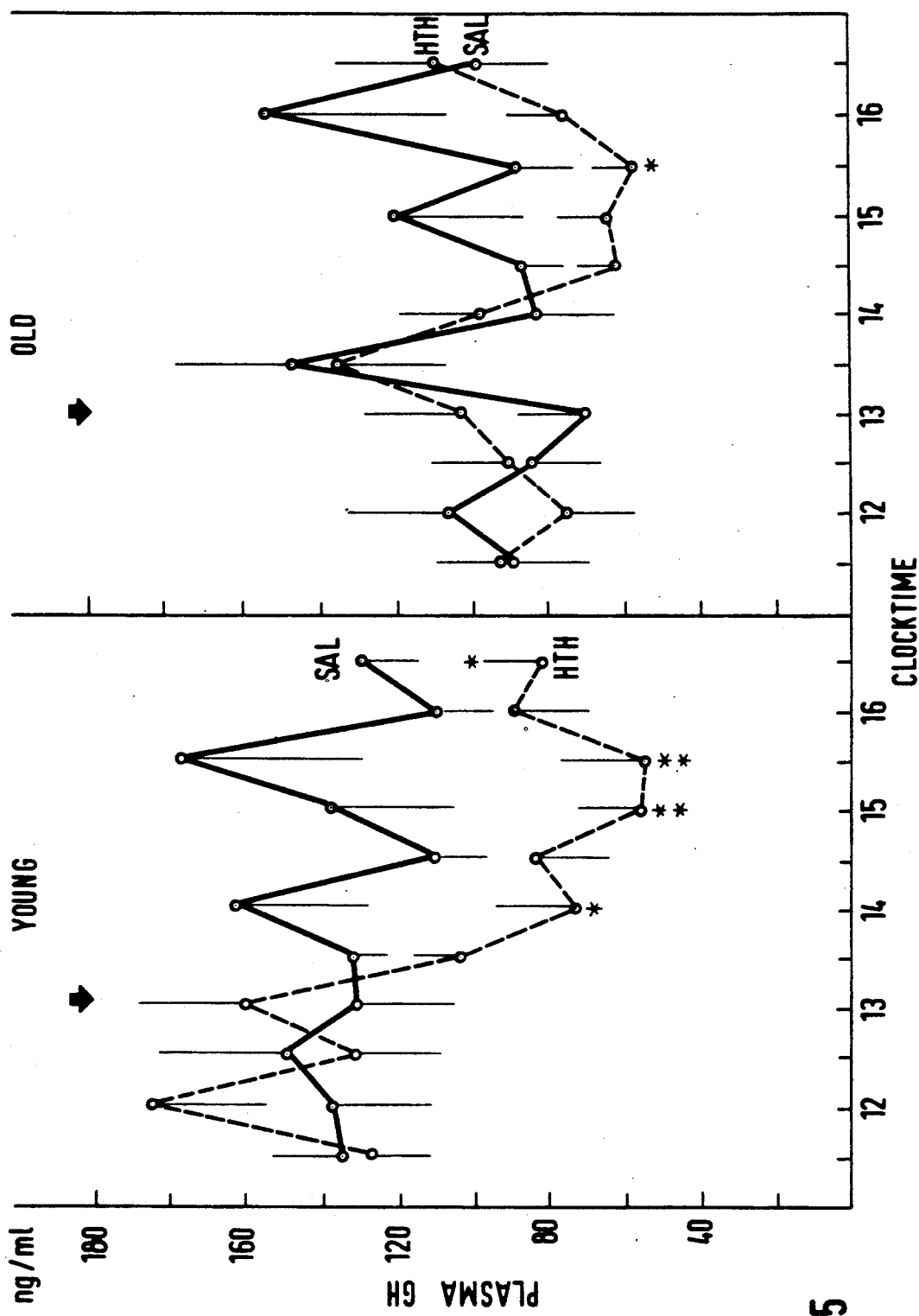

Differential effect of histone dimer H2A:H2B on plasma thyrotropin and growth hormone in young and old rats The histone H2A:H2B dimers reduces plasma thyrotropin (TSH) and growth hormone (GH) in young (3 mo) Sprague-Dawley male rats, but fails to do so (TSH) or has a significantly weaker effect (GH) in old (28 mo) animals. Young and old conscious, free-moving rats carrying an indwelling strial cannula received the substances to be tested via the cannulas. Plasma samples were taken every 30 min. for 5 h and hormones were measured by RIA. In the young rats histone H2A:H2B (9 mg/kg B.W.) induced a marked reduction in plasma TSH which was significantly greater than the normal circadian decline observed in saline-injected young controls. The old rats displayed high basal levels of TSH which showed no circadian rhythmicity and did not respond to histones H2A and H2B. Plasma thyroxin ($T_4$) showed a significant age-related reduction but was not affected by histones. The above dose of H2A:H2B significantly reduced plasma GH in both young and old rats, but the effect was greater in this young animals. Mean basal levels of plasma GH were significantly lower in old than in young rats. The present results suggest that histones $H_2A$ and $H_2B$, whose production by the thymus is known to be stimulated by TSH and GH, is involved in an inhibitory feedback loop regulating plasma TSH and GH in young rats. The present date also add to the growing evidence that the immune and the neuroendocrine systems function coordinately. The results additionally suggest that a disruption in immuno-neuroendocrine integration occurs during aging. This disruption could play a significant role in the age-associated immunopathologies that occur in both humans and laboratory animals (FIGS. 4 and 5).

EXAMPLE 4

Figure 6:
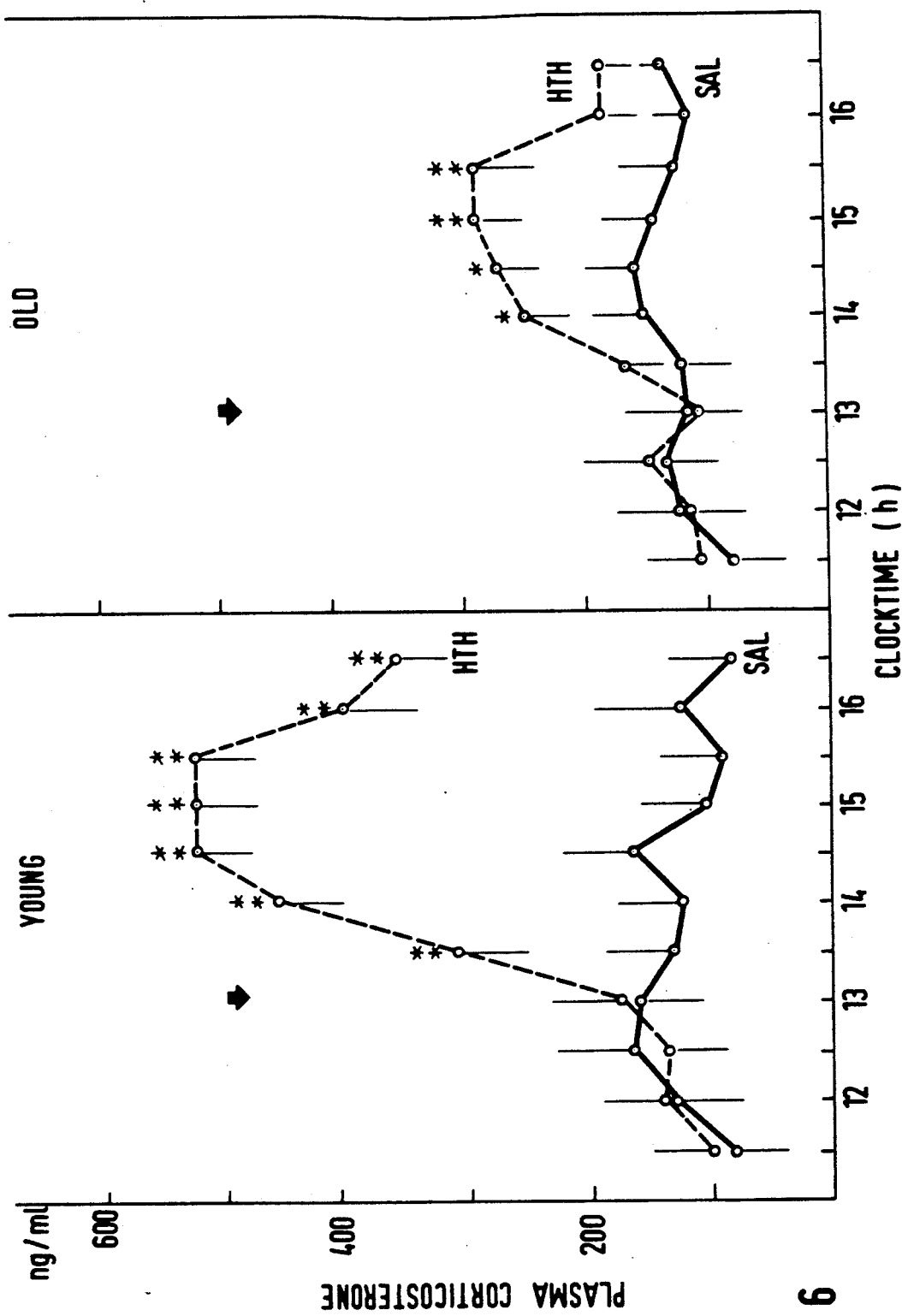

Histone H2A:H2B dimer increases plasma levels of corticosterone but not prolactin (Prl) in a dose- and age-dependent manner in male Sprague-Dawley rats. Young (3 mo) and old (26 mo) conscious free-moving animals carrying an indwelling atrial cannula received the substances to be tested via the cannulas. Plasma samples were taken every 30 min. for 5 h and hormones were measured by RIA. Histone doses of 1 and 8 mg/kg B.V. injected into young rats elicited a 7,8- or 12,8-fold increase in plasma corticosterone, respectively, as compared to saline-injected controls. The histone-induced peak corticosterone levels were reached within 1.5 and 2,5 h after 2,5 h after H2A:H2B injection. Plasma Prl was not affected by the histones in either age group. A single dose of 8 mg H2A:H2B/kg B.W. induced a smaller corticosterone response in old than in young rats. Although the time course of the response was similar in both age-groups. Depending on the now known activities of histones H2A and H2B the present results add to the growing evidence that the immune and neuroendocrine systems function coordinately. The data also suggest that a disruption in immune-neuroendocrine integration occurs during aging. This disruption could play a significant role in age-associated immuno-pathologies, particularly autoimmunity (FIG. 6).

Preparation of H1 Histones

Thymus Tissue

Thymus glands from calf were commercially obtained by slaughter houses. Glands taken directly from animals were immediately frozen on dry ice and stored at −30° C.

Isolation of Nuclei

Whole glands were cut to pieces and homogenized in three volumes of 0.3M sucrose containing 3 mM $CaCl_2$. The homoganate was centrifuged for 10 minutes at 200 g. The combined crude pellets were homogenized in 10 volumes of 2.5M sucrose. 3 mM $CaCl_2$ and centrifuged for 60 min at 45 000 g. The pellets containing the nuclei were combined and washed twice with 0.5M sucrose, 3 mM $CaCl_2$ and once with 0.15M NaCl, 10 mM EDTA. After each step of washing the pellets were centrifuged at 1000 g for 10 min.

Preparation of H1 Histones

Total histones (H1, H2A, H2B, H3, H4) were extracted from the combined nuclear pellets by treatment with 0,4N $H_2SO_4$ at 0° C. for 15 h. The mixture was centrifuged at 70 000 g for 30 min, 5 vol. of cooled ethanol was added to the supernatant, and the mixture was stood overnight at −20° C., H1 histones were extracted from the mixture with 5% perchloric acid for 3 h, and the mixture was centrifuged at 200 g for 10 min subsequently. The supernatant was dialyzed against 1 mM acetic, acid overnight. H1 histone was precipitated by the addition of 100% trichloroacetic acid (1 gm/ml) to a final concentration of 20% at 0° C. After 15 min the precipitate was collected by centrifugation at 3 500 HCl/100 ml) and twice with acetone. After centrifugation at 500 g for 10 min the pallets were soluted in 1 mM acetic acid and lyophilized to obtain H1 histones.

EXAMPLES 5 TO 10

The action of Histone H1 was tested in vitro on six human cancer cell lines originating from B-cells of the lymphatic system. The concentration of H1 tested was 250 mcg/ml medium for the following cancers strains: Daudi, EB 2, CCRF SB, CCRF CEM and Namalwa and 180 mcg/ml for the IM9 strain. A maximal decay of cancer cells was observed between the $3^{rd}$ and $6^{th}$ day and reached up to 100%. A cancer cell lines began to grow again, but did not reach the initial cell concentration. The treatment of normal spleen cells of mice showed that H1 had no significant toxicity on these cells at a concentration of 50-200 mcg/ml under the conditions employed.

Materials and Methods

Cell lines:

DAUDI: Burkitt Lymphoma of a 16 year old negro. Translocation of parts of the chromosomes 8 and 15 led to the activation of an oncogene. There are binding sites for the fc-receptor and for receptors for complement and immunglobulins.

EB2: Burkitt Lymphoma of a 7 year old negro. The line contains free active Epstein-Barr virus particles.

IM9: Myelogenic Leucemia of a female patient. The cell line is able to produce IgG. There are receptors for human growth factors, insulin and calcitonin.

CCRF SB: B-lymphoblastic Lymphoma of a 11 year old caucasic girl. The line is not able to produce IgG.

CCRF CEM: B-lymphoblastic Lymphoma of a 4 year old caucasic boy. The line is able to produce IgG. No common receptors are B-cells on the membranes.

Namalwa: Burkitt Lymphoma

The tested cell lines were obtained from FLOW Lab. and grew in RPMI-1640 medium with 10% FCS in a humidifed incubator with 5.5% $CO_2$. $2 \times 10^5$ cells/ml medium were incubated with 180-250 mcg hormone/ml and spread in 96 well dishes. The viable cells were counted by the ethidium bromide and acridine orange method. (6B/A0).

EXAMPLE 5

DAUDI showed a 96% decay of cells after two days and had 20% viable cells at the end of the experiment (FIG. 7).

EXAMPLE 6

EB2 showed a continuous dying of cells up to the 6th day and had 70% vital cells at least (FIG. 8).

EXAMPLE 7

IM9 cells were very sensitive and showed a survival rate below 10% within 3 days. After 6 days no living cells were observed (FIG. 9).

EXAMPLE 8

CCRF SB: A maximal death rate of 58% of the cells was observed on the 3rd day. On the 6th day the cells grew up to 80% of the initial cell concentration (FIG. 10).

EXAMPLE 9

CCRF CEM: On the 5th day about 95% of the cells were killed and on the 6th day a slight growth had occured to about 20% of the initial cell concentration (FIG. 11).

EXAMPLE 10

Namalwa was also very sensitive against H1 I and showed a maximal decay rate of 99% after 4 days. Little growth occured on day 5 and day 6 (2% of the initial cell concentration) (FIG. 12)

To summarize, Histone H1 was cytoxic against all tested human cancer cells when it was applied as a single dose at a concentration of 180/250 mcg/ml. The cell line IM9 was the most sensitive one and was completely killed within 6 days. Three of the tested cell lines were Burkitt Lymphomas (Daudi, Namalwa & EB2). While more than 95% of the Daudi and Namalwa cells were killed, EB2 cells represent the most resistant cell line (death rate 30%). It is possible that this behaviour depends on the presence of EB-Virus particles. Both CCRF SB and CCRF CEM showed approximately 50% death rate on the $3^{rd}$ day. While the number of living cells of CCRF CEM was about 5% on day 5, the cells of CCRF SB were growing again from day 2 and reached about 80% of living cells in compared to the initial cell concentration (FIG. 13).

FIG. 14 shows the viability of normal murine spleen cells as function of H1-concentration from 50 μg/ml to 200 μg/ml.

EXAMPLE 11

Lymphoma

Figure 15:
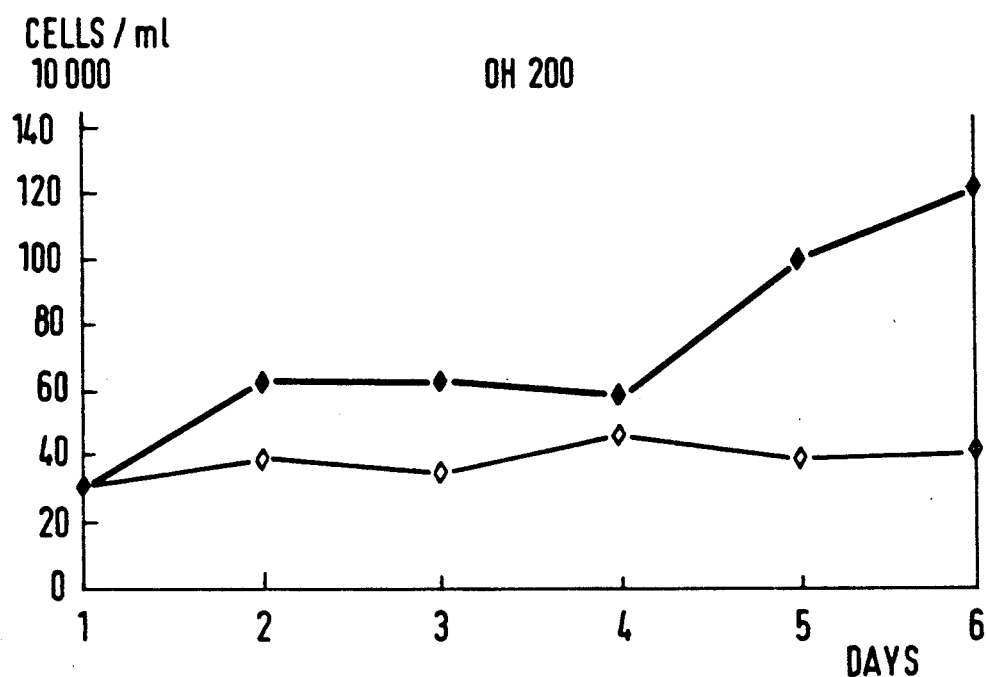

The cell line OH was obtained from a patient of the University Hospital of Lund, Department of Lund Medicine, and cultured as described in Example 1 except the cell density which was adjusted to 315 cell per se. Incubation with a single dose of 200 mg H1 Histone almost completely arrested the growth of the cells, whereas the control grew from $3 \times 10^5$ cells perml to $1,2 \times 10^6$ cells per ml within six days (FIG. 15; (OH200))

EXAMPLE 12

Melanoma

Figure 16:
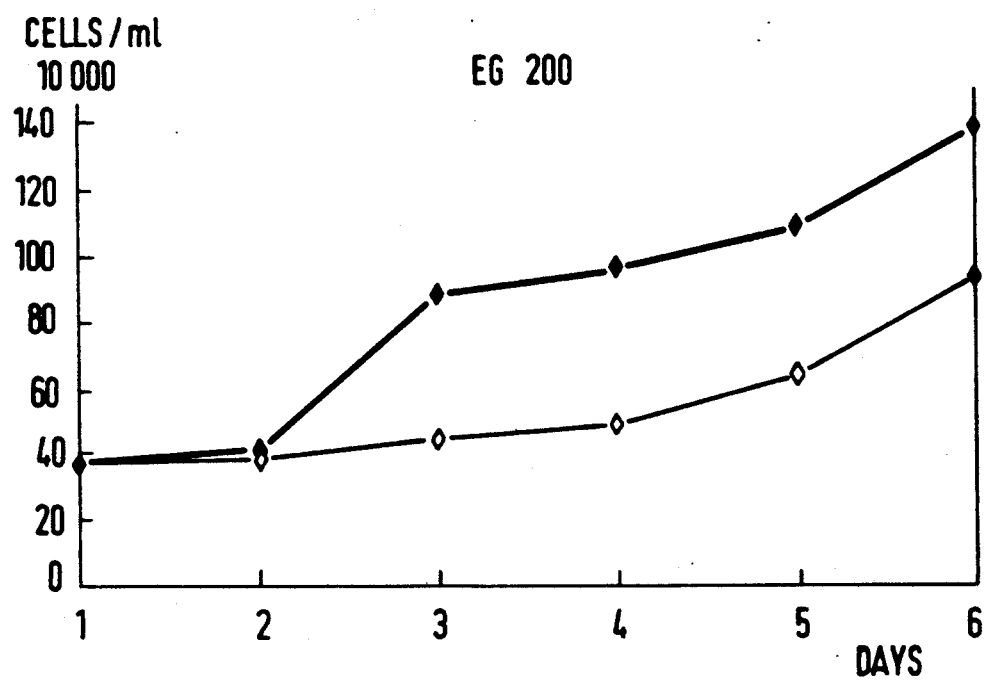

The cell line E6 was obtained from the University Hospital of Lund and cultivated as described in Example 1. The first day of incubation with a single dose of 200 mg per ml of histone H1 the cell density was determined to $40 \times 10^4$ cells per ml. In the sample 1 treated with histone H1 the cell number stayed roughly constant until day four and increased to $90 \times 10^4$ cells per ml at day 6. In the control the number of cells increased to $90 \times 10^4$ cells per ml at day 3 and to $140 \times 10^4$ cells per ml at day 6 (FIG. 16; (EG 200)).

EXAMPLE 13

Sarcoma

Figure 17:
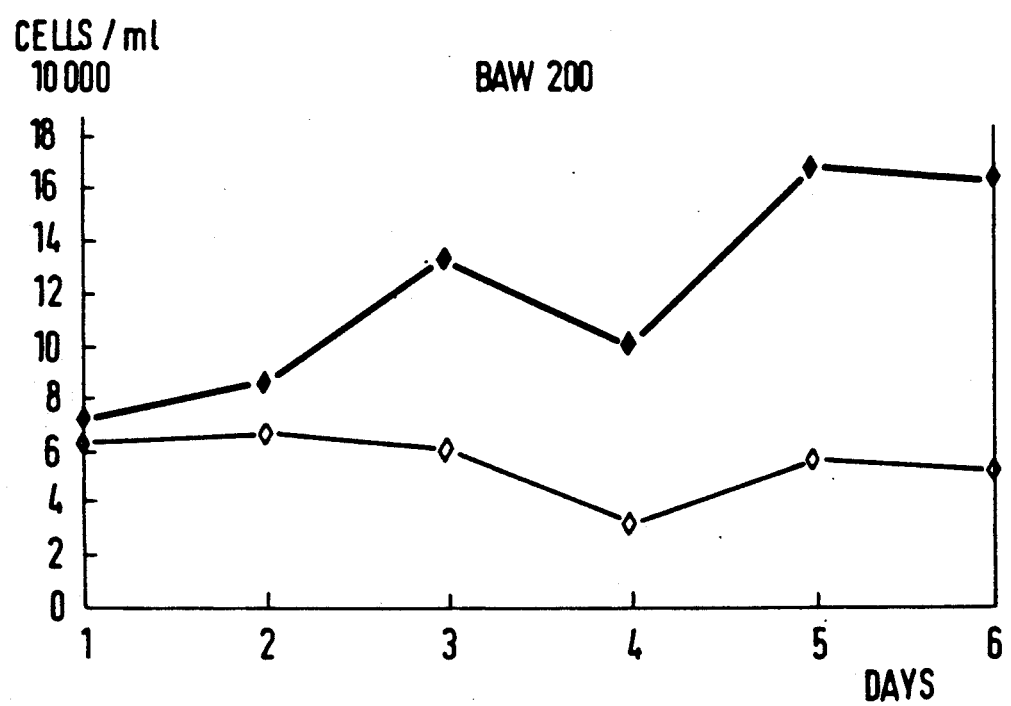

The cell line BAW was obtained from a patient of the University Hospital at Lund and cultivated as described in Example 1. The cell density was determined to $6 \times 10^4$ cells per ml in the experiment and to $7 \times 10^4$ viable cells per ml in the control immediately upon incubation with 200 mg per ml histone H1. As shown in FIG. 17 (BAM 200) after day 5 the number of viable cells had decreased below $5 \times 10^4$ cells per ml whereas the untreated control had increased to about $17 \times 10^4$ cells per ml.

We claim:

1. A therapeutic method for treatment of radiation-induced leukemia or carcinoma of a patient in need thereof which comprises administering to said patient a biological composition which comprises a therapeutically acceptable carrier and, in a quantity having a therapeutic effect, a biologically active pure histone consisting of H1 or histone dimer H2A:H2B.

2. The therapeutic method of claim 1, wherein the treatment is for one of the following: melanoma, sarcoma, malignant B- and T-cells such as B-lymphoblastic lymphoma, and Burkitt-lymphoma.

3. The method of claim 1, wherein the source of the pure active histone is selected from one of the following: an endocrine gland of an animal or the gland of a calf thymus.

4. The method of claim 1, wherein the biological composition includes a protein of the immuno system.

5. The method of claim 1, wherein the biological composition includes ubiquitin.

6. A biologically active composition, which comprises a physiologically acceptable carrier and pure histone H1.

7. The biologically active composition of claim 6 having anti-carcinoma activity.

8. The biologically active composition of claim 6, wherein the pure active histone is extracted from one of the following: an endocrine gland of an animal or the gland of a calf thymus.

9. The biologically active composition of claim 6 which includes one a protein of the immuno system.

* * * * *